United States Patent [19]
Quinn

[11] Patent Number: 5,938,083
[45] Date of Patent: Aug. 17, 1999

[54] INTEGRAL NEBULIZER STAND AND CARRIER GAS CONDUIT

[75] Inventor: Brad Quinn, Indianapolis, Ind.

[73] Assignee: Engineered Medical Systems, Inc., Indianapolis, Ind.

[21] Appl. No.: 08/874,700

[22] Filed: Jun. 13, 1997

[51] Int. Cl.$^6$ ........................................................ B67D 5/06
[52] U.S. Cl. ........................ 222/186; 222/184; 248/205.5; 248/205.9
[58] Field of Search ............................... 222/181.1, 181.2, 222/181.3, 185.1, 184, 186; 248/205.5, 205.9

[56] References Cited

U.S. PATENT DOCUMENTS

| | | |
|---|---|---|
| 1,485,345 | 2/1924 | Fleming . |
| 1,985,502 | 12/1934 | Isenberg ................................ 248/205.5 |
| 2,072,345 | 3/1937 | Schneider . |
| 2,174,653 | 10/1939 | Conklin . |
| 2,216,149 | 10/1940 | Weiss . |
| 2,893,644 | 7/1959 | Holden . |
| 3,228,613 | 1/1966 | Goldstein . |
| 3,353,536 | 11/1967 | Bird et al. . |
| 3,395,703 | 8/1968 | Chouinard et al. . |
| 3,762,409 | 10/1973 | Lester . |
| 4,351,327 | 9/1982 | Rinne et al. . |
| 4,463,754 | 8/1984 | McDonald . |
| 4,512,341 | 4/1985 | Lester . |
| 4,566,452 | 1/1986 | Farr . |
| 5,040,756 | 8/1991 | Via Cava . |
| 5,318,015 | 6/1994 | Mansson et al. . |
| 5,507,460 | 4/1996 | Schneider . |

*Primary Examiner*—Andres Kashnikow
*Assistant Examiner*—David Deal
*Attorney, Agent, or Firm*—Swanson & Bratschun LLC

[57] ABSTRACT

An integral stand and fluid conduit for maintaining a housing of a fluid delivery device in a select orientation relative to a support surface. The fluid delivery device has a carrier fluid connector fixedly attached to its housing. The carrier fluid connector extends along an axis away from the housing for axial engagement in fluid communication with a carrier fluid supply. The stand includes a base having a support surface engaging portion. A conduit having an inlet and an outlet is attached to the base. The inlet is connectable in fluid communication with a carrier fluid supply and the outlet extends from the base such that with the support surface engaging portion of the base engaging a support surface, the conduit outlet is axially engagable with the carrier fluid connector of the fluid delivery device to thereby bias the fluid delivery device to the select orientation relative to the support surface. A support surface adhesion member such as a suction cup is provided on the support surface engaging portion of the base. The base, the conduit and the support surface adhesion member are integrally formed from a single piece of an elastomer.

17 Claims, 2 Drawing Sheets

INTEGRAL NEBULIZER STAND AND CARRIER GAS CONDUIT

BACKGROUND OF THE INVENTION

1. Technical Field

The present invention is directed to a stand for a fluid delivery device, and more particularly toward an integral stand and carrier gas delivery conduit for maintaining a nebulizer in a select orientation.

2. Background Art

Nebulizers are devices for delivering atomized water or medication to air to be inhaled into the lungs of a patient. Most nebulizers are connected in series with a device to supply pressurized air to the patient and the nebulizers have a reservoir to contain the liquid (or in some cases, powder) medication. A variety of nebulizer structures are known in the medical field. An exemplary nebulizer is that disclosed in Lester, U.S. Pat. No. 3,762,409. The nebulizer described in Lester '409 provides an acorn-shaped reservoir so that as the liquid is consumed it is drained toward the converging bottom to the point of the acorn where a liquid inlet to the nebulizer system is located.

Typically a nebulizer of the type described in Lester '409 is used for delivering medication in the form a finely nebulized mist to a patient. Often this medication must be delivered in precise dosages. It is also common for the liquid medication being delivered to be very expensive, costing as much as $100/cc. A nebulizer such as that disclosed in Lester '409 introduces substantially all the liquid medication is introduced into the air supply of the patient if the nebulizer is kept in a vertical orientation. However, often nebulizers are tipped out of their vertical orientation, causing a nebulizer such as that disclosed in Lester '409 to not deliver all the liquid medication to a patient.

Farr, U.S. Pat. No. 4,566,452 is another exemplary prior art nebulizer structure. Farr discloses a nebulizer having a nebulizer top and a reservoir bottom which are threadably connectable to define a nebulizer housing. A gas jet extends from the reservoir bottom along a longitudinal axis of the reservoir bottom. A liquid spray nozzle surrounds the gas jet defining a passageway for liquid between the gas jet and the liquid nozzle. At the top of the gas jet is a gas orifice which leads into a space in fluid communication with the spray nozzle passage way. A second orifice in the top of the spray nozzle is axially aligned with the orifice in the gas jet. A diffuser is connected to the nebulizer top and spaced from the nozzle orifice with the nebulizer top and reservoir bottom threadably connected. As gas is caused to flow through the gas jet, a vacuum is formed in the space between the gas orifice and the nozzle orifice, drawing fluid for nebulization to the fluid nozzle orifice. Nebulized fluid impinges upon the diffuser, causing oversized droplets to stick to the diffuser and providing a finely nebulized mist for delivery to the lungs of a patient.

Farr addresses the problem of delivering substantially all of a measured amount of medication to the lungs of a patent by providing an extended side which projects outwardly from the spray nozzle and is adapted to fit snugly within the interior of the nebulizer bottom to define a space between the extended side and the inner surface of the side wall. This space functions as a conduit to deliver fluid to the fluid nozzle even when the nebulizer is tipped from its normal vertical orientation.

Lester, U.S. Pat. No. 5,512,341, is also directed to a structure for delivering substantially all of a measured volume of liquid to a patient even when the nebulizer is tipped from its vertical orientation. Lester '341 has the same basic housing structure of Farr and further discloses a plate that overlies the bottom of the nebulizer reservoir to define a capillary channel for delivering fluid to the nozzle when the nebulizer is tipped.

While the structures of Farr and Lester '341 are useful for delivering liquid medication through a nebulizer when the nebulizer is tipped from its vertical orientation, these structures are not without serious problems. Most notably, in order to maintain flow to the fluid nozzle, very close tolerances must be maintained within the nebulizers. This significantly increases the cost of the nebulizers and can create quality control problems.

The nebulizers disclosed in Farr and Lester '341 have a carrier gas supply connector which extends along a vertical axis downward from the reservoir bottom of the nebulizer housing. In order to enable the nebulizer bottom to be conveniently filled, Farr provides legs extending downward from the bottom of the housing to support the nebulizer housing in an upright position on a horizontal surface during loading. Similarly, Lester provides an annular collar around the carrier gas connector to maintain it upright during loading. One additional problem with this type of structure, however, is that during loading, the medical professional must be extremely careful not to tip the nebulizer bottom or expensive medications can be wasted. This problem can be exacerbated during emergency situations such as when the medical professional must move very quickly in a distracting environment.

The present invention is directed to overcoming one or more of the problems discussed above.

SUMMARY OF THE INVENTION

The present invention is directed to a stand for maintaining a housing of a fluid delivery device such as a nebulizer in a select orientation relative to a support surface. The fluid delivery device has a carrier fluid connector fixedly attached to its housing. The carrier fluid connector extends along an axis away from the housing for axial engagement in fluid communication with a carrier fluid supply. The stand includes a base having a support surface engaging portion. A conduit having an inlet and an outlet is attached to the base. The inlet is connectable in fluid communication with a carrier fluid supply. The outlet extends from the base such that with the support surface engaging portion of the base engaging a support surface, the conduit outlet is axially engagable with the carrier fluid connector of the fluid delivery device to thereby bias the fluid delivery device to the select orientation relative to the support surface.

A support surface adhesion member such as a suction cup may be provided on the support surface engaging portion of the base. Preferably, the base, the conduit and the support surface adhesion member are integrally formed of a single piece of an elastomer. In one particular embodiment of the invention, the conduit is attached to the base with the outlet along a vertical axis with the support surface engaging portion of the base engaging a horizontal support surface. In this manner, the stand can axially receive a carrier fluid connector which extends vertically downward from a fluid delivery device in its upright orientation and maintain the fluid delivery device in its upright orientation relative to the horizontal support surface.

The fluid delivery device stand of the present invention maintains a fluid delivery device such as a nebulizer in a select operative orientation. In this manner, the stand ensures that liquid medication intended for delivery to a patient is in fact so delivered. Thus, the stand not only facilitates delivery of precisely measured amounts of fluid to a patient, the stand ensures that expensive medications will not be wasted. The stand also stabilizes a nebulizer reservoir during loading of the reservoir to minimize the risk of spillage. The preferred embodiment of this stand is made of an elastomer, which enables a clinician to tap the nebulizer during administration of a medication to help dislodge drops of medication which might be adhering to the sidewall of a reservoir to deliver the droplets for administration to a patient. Similar advantages are also obtainable with a nebulizer for delivering fine powders to a patient, such as that disclosed in Riggs, U.S. Pat. No. 5,355,872. In addition, the device can be readily made in a number of configurations to properly orient a nebulizer with respect to horizontal support surface, a vertical support surface, or support surfaces at any angle therebetween. The stand can be quickly and easily connected to a nebulizer by a medical professional, therefore making it convenient and easy to use. Moreover, the preferred embodiment of the stand is quickly and easily injection molded from a medical grade elastomer such as PVC, natural rubber, thermoplastic rubber, silicon rubber or the like, making it extremely inexpensive to manufacture.

DETAILED DESCRIPTION OF THE PREFERRED EMBODIMENT

Figure 1:
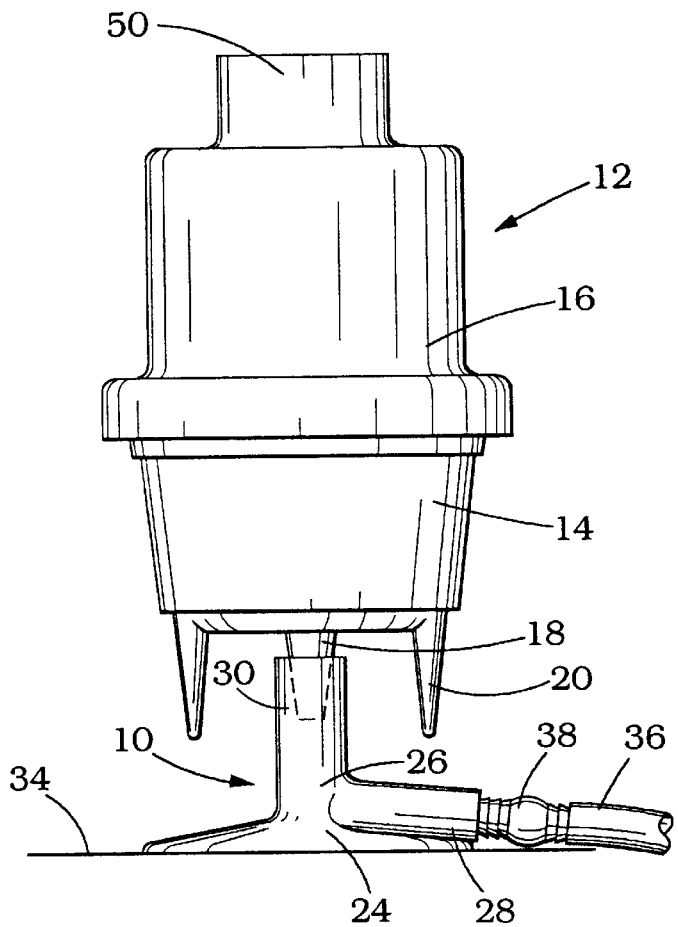
FIG. 1 is an elevational view of the nebulizer stand of the present invention operatively engaged with a vertical, downward extending carrier gas connector of a nebulizer.

An integral nebulizer stand and carrier gas conduit 10, which hereinafter will be referred to simply as a nebulizer stand 10, is shown in operative engagement with a conventional nebulizer 12. While the present description of the preferred embodiment is directed toward a nebulizer stand 10 used with a nebulizer 12, the invention contemplates a nebulizer stand 10 being usable with any fluid or powder delivery device connectable to a carrier fluid source.

The nebulizer 12 consists of a reservoir bottom 14 and a nebulizer top 16 which together form the nebulizer housing. A carrier gas inlet connector 18 extends vertically downward from the reservoir bottom 14 along the longitudinal axis of the nebulizer 12. A plurality of legs 20 extend from the lower surface of the reservoir bottom 14 beyond the end of the carrier gas connector 18 so that the reservoir bottom 14 can be set on a horizontal planar surface during addition of liquid medication, storage and the like. Details of the structure and operation of exemplary conventional nebulizers can be found in Farr, U.S. Pat. No. 4,566,452; Lester, U.S. Pat. No. 4,512,341; or Lester, U.S. Pat. No. 3,762,409, the disclosures of which are hereby incorporated by reference.

Figure 2:
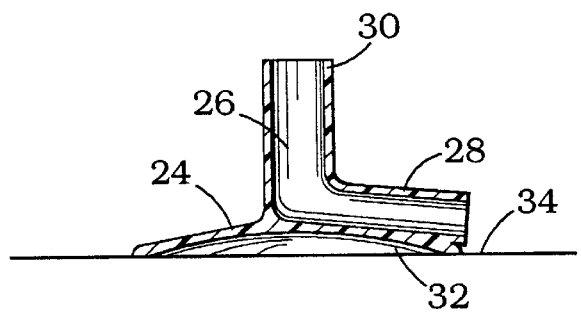
FIG. 2 is a sectional, elevational view of the nebulizer stand of FIG. 1.
Figure 3:
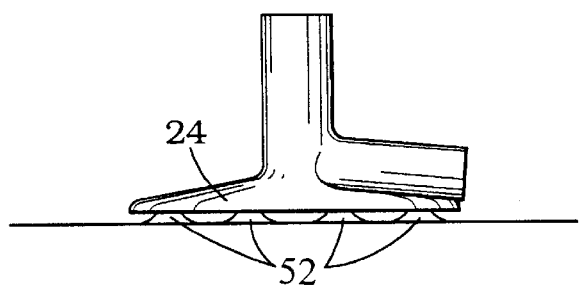
FIG. 3 is an elevational view of an alternate embodiment of the nebulizer stand of FIG. 1.
Figure 4:
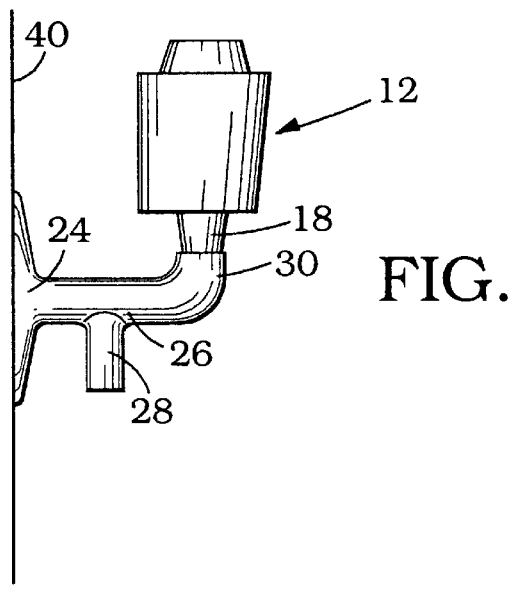
FIG. 4 is an elevational view of a second alternate embodiment of the nebulizer stand of the present invention operatively engaged with a vertical, downward extending carrier gas connector of a nebulizer.
Figure 5:
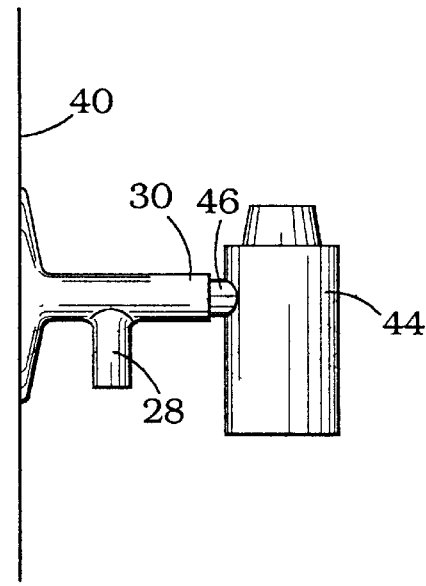
FIG. 5 is a third alternate embodiment of the nebulizer stand of the present invention operatively engaged with a horizontally extending carrier gas connector of a nebulizer.
Figure 6:
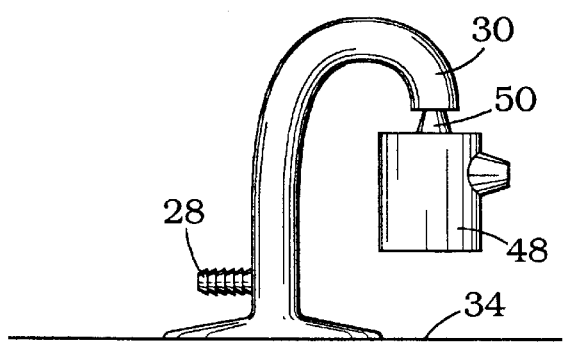
FIG. 6 is a fourth alternate embodiment of the nebulizer stand of the present invention operatively engaged with a vertical, upward extending carrier gas connector of a nebulizer.

The nebulizer stand 10 consists of a base 24 and an integral conduit 26 having an inlet 28 and an outlet 30. As perhaps best seen in FIG. 2, the inlet 28 of the conduit 26 is along a substantially horizontal axis whereas the outlet 30 is along a substantially vertical axis. The bottom of the base 24 defines a support surface engaging portion 32. The support surface engaging portion 32 in FIG. 2 is in the form of a suction cup for adhering the base to a horizontal support surface 34. Alternatively, the horizontal support surface could be coated with an adhesive or the like to adhere it to a support surface. The conduit 26, the base 24 and the support surface engaging portion or suction cup 32 are preferably integrally molded from a single piece of a suitable medical grade elastomer, such as PVC, rubber, thermoplastic rubber, silicon rubber or the like. The essential properties of the selected elastomer are that it be sufficiently rigid to maintain a nebulizer 12 engaged with the nebulizer stand 10 in the select orientation as depicted in FIG. 1 and that it be sufficiently resilient to bias the nebulizer 12 back to the select orientation upon the nebulizer being subjected to horizontal forces, such as by tapping by a user. In addition, the elastomer must be sufficiently flexible to enable the suction cup to adhere firmly to a non-porous surface.

As illustrated in FIG. 1, the carrier gas connecter 18 of the nebulizer 12 is axially, telescopingly received within the outlet 30. Connection is then made to a source of a carrier gas (not shown) by a tube 36 which is connected to the inlet 28 by an adaptor 38. The adaptor 38 has a number of annular barbs along its longitudinal axis to facilitate firm telescoping receipt within the inlet 28 and the tube 36. Alternatively, the inlet 28 could be provided with integrally formed annular barbs as illustrated in FIG. 6. Any other form of connector, such as a leur connector, could also be used. In one preferred embodiment (not shown), the tube 36 is solvent bonded directly to the inlet 28 by a suitable solvent such as methylene chloride. Heat staking or other such bonding methods may also be used.

FIG. 3 shows an alternate embodiment of the nebulizer stand of FIG. 1 wherein the surface engaging portion is a plurality of suction cups 58 extending from the base 24, as opposed to a single suction cup as illustrated in FIGS. 1 and 2.

FIG. 4 illustrates a second alternate embodiment for maintaining a nebulizer such as that depicted in FIG. 1 having a vertically downwardly extending carrier gas connector 18 in a select orientation with respect to a vertical support surface 40. As should be readily apparent, the angle the outlet portion 30 of the conduit 26 extends from the base could be varied to maintain the nebulizer 12 in its proper orientation regardless of the angle of the support surface.

FIG. 5 illustrates a third alternate embodiment of a nebulizer stand for maintaining a nebulizer 44 having a horizontally extending carrier gas connector 46 in an upright orientation with respect to a vertical support surface 40.

FIG. 6 is a fourth alternate embodiment of a nebulizer stand for maintaining a nebulizer 48 having an upwardly extending carrier gas connector 50 in a vertical orientation with regard to a horizontal support surface 34.

FIGS. 1–6 illustrate merely some of the many permutations of configurations of nebulizer stands incorporating the inventive concept and should not be considered limiting the scope of the inventive concept.

Referring to the embodiment illustrated FIG. 1, in use, the carrier gas connector 18 is axially inserted into the outlet 30 of the nebulizer stand 10. The nebulizer stand 10 can then be adhered to a non-porous horizontal support surface 34 by pressing the suction cup 32 into contact with the support surface 34. When thus connected, the reservoir bottom 14 is biased to its upright position. Liquid medication can then be added to the reservoir bottom 14 without concern for tipping. The tube 36 extending from a source of pressurized carrier gas is then connected to the carrier inlet 28. The nebulizer top 16 can then be secured in place and a nebulizer outlet 50 placed in fluid communication with a respiratory circuit, not shown.

When assembled in this manner, the nebulizer 12 is maintained in its upright, vertical orientation by the nebulizer holder 10. Because the nebulizer stand 10 is made of an elastomeric material, the nebulizer 12 can be tapped by the user to dislodge droplets of medication which may adhere to the inner surface of the reservoir bottom 14 to ensure delivery of substantially all the liquid medication to a patient, and the nebulizer will be biased back to its upright orientation. These significant advantages are achieved by a nebulizer holder which can be integrally formed in a single injection molding step, meaning that the nebulizer holder 10 can provide these advantages at a low cost.

What is claimed is:

1. A stand for maintaining a housing of a fluid delivery device in a single select orientation relative to a support surface, the fluid delivery device having a carrier fluid connector fixedly attached to the housing, the carrier fluid connector extending along an axis away from the housing for axial engagement in fluid communication with a carrier fluid supply, the stand comprising:
   a base having a support surface engaging portion; and
   a conduit having an inlet and an outlet, the inlet being connectable in fluid communication with a carrier fluid supply and the conduit being attached to the base with the conduit outlet oriented relative to the base such that with the support surface engaging portion of the base engaging the support surface, the conduit outlet is axially engagable with the carrier fluid connector of the fluid delivery device with the fluid delivery device in the single select orientation and the fluid delivery device is thereby biased to the single select orientation relative to the support surface.

2. The stand of claim 1 further comprising a support surface adhesion member on the base.

3. The stand of claim 2 wherein the support surface, the base, the conduit and the support surface adhesion member are integrally formed of a single piece.

4. The stand of claim 3 wherein the base, the conduit and the adhesion member are formed of an elastomer.

5. The stand of claim 2 wherein the support surface adhesion member is a suction cup.

6. The stand of claim 1 wherein the base and conduit are integrally formed of a single piece.

7. The stand of claim 6 wherein the base and the conduit are formed of an elastomer.

8. The stand of claim 1 wherein the carrier fluid connector extends downward from the housing along a vertical axis with the fluid delivery device in the select orientation relative to a horizontal support surface and the conduit is attached to the base with the outlet along a vertical axis with the support surface engaging the horizontal support surface.

9. The stand of claim 8 wherein the conduit inlet is along a second axis which is at substantially a right angle with the outlet axis.

10. A stand for maintaining a housing of a fluid delivery device in a single select orientation relative to a horizontal support surface, the fluid delivery device receiving a carrier fluid from a pressurized carrier fluid supply through a carrier fluid connector extending downward from the housing along a vertical axis with the housing in the single select orientation relative to the horizontal support surface for axial connection to a carrier fluid supply, the stand comprising:
    a base having a bottom for engaging a horizontal support surface; and
    a conduit attached to the base, the conduit having an inlet and an outlet, the inlet being connectable in fluid communication with a carrier fluid supply and outlet extending along an axis substantially normal to the horizontal support surface with the base bottom engaging the horizontal support surface, the conduit outlet being axially engagable with the carrier fluid connector of the fluid delivery device to bias the fluid delivery device to the single select orientation with the base bottom engaging the horizontal support surface.

11. The stand of claim 10 further comprising a support surface adhesion member on the base bottom.

12. The stand of claim 11 wherein the support surface adhesion member comprises a suction cup.

13. The stand of claim 12 wherein the base, the conduit and the suction cup are integrally formed of a single piece of elastomer.

14. The stand of claim 11 wherein the support surface adhesion member comprises a plurality of suction cups.

15. The stand of claim 10 wherein the base and conduit are integrally formed of a single piece.

16. The stand of claim 15 wherein the base and conduit are formed of an elastomer.

17. A stand for maintaining a housing of a nebulizer in a single select orientation relative to a horizontal support surface, the nebulizer having a gas connector extending along an axis vertically downward from the housing with the housing in the single select orientation, the gas connector being axially engagable with a carrier gas supply, the stand comprising:
    a base having a bottom with at least one suction cup attached thereto for engaging a horizontal support surface; and
    a conduit integrally formed from a single piece of elastomer with the base and the suction cup, the conduit having an inlet and an outlet, the inlet being connectable in fluid communication with a carrier gas supply and the outlet extending along an axis substantially normal to the horizontal support surface with the base bottom engaging the horizontal support surface, the conduit outlet being configured to axially engage the gas connector of the nebulizer, the stand thereby biasing the nebulizer housing to the single select orientation with the base bottom engaging the horizontal support surface.

* * * * *